| United States Patent [19] | [11] Patent Number: 4,871,837 |
| Magnusson et al. | [45] Date of Patent: Oct. 3, 1989 |

[54] HYDROXY PROTECTION GROUPS

[75] Inventors: Hans G. Magnusson; Karl Jansson, both of Lund, Sweden

[73] Assignee: Symbicom Aktiebolag, Umea, Sweden

[21] Appl. No.: 7,330

[22] Filed: Jan. 27, 1987

[30] Foreign Application Priority Data

Jan. 27, 1986 [DK] Denmark ............................... 398/86

[51] Int. Cl.$^4$ ........................ C08F 297/02; C07H 5/06
[52] U.S. Cl. .................................... 536/4.1; 536/17.1; 536/17.2; 536/18.6
[58] Field of Search ...................... 536/17.1, 4.1, 17.2, 536/18.6

[56] References Cited

U.S. PATENT DOCUMENTS

| 4,143,089 | 3/1979 | Martin | 525/271 |
| 4,273,896 | 6/1981 | Martin | 525/271 |
| 4,694,076 | 9/1987 | Ogawa et al. | 536/4.1 |

*Primary Examiner*—Ronald W. Griffin
*Attorney, Agent, or Firm*—Iver P. Cooper

[57] ABSTRACT

The present invention concerns a method for preparing unprotected hydroxy compounds or acylated derivatives thereof by conversion of silyl alkyl-protected hydroxy compounds. The invention also relates to novel intermediates useful in the method and for other purposes.

28 Claims, No Drawings

HYDROXY PROTECTION GROUPS

BACKGROUND OF THE INVENTION

The present invention concerns a method for preparing unprotected hydroxy compounds or acylated derivatives thereof by conversion of silyl alkyl-protected hydroxy compounds. The invention also relates to novel intermediates useful in the method and for other purposes.

Within certain fields of synthetic chemistry, in particular within the field of preparation of glycosides, there exists a need for methods and intermediates making possible easy and high-yielding preparation of e.g. oligosaccharides and glycosides. Thus, the availability of e.g. suitably protected sugar "building blocks" and reactions capable of joining such "building blocks" on the one hand with one another and on the other hand with suitable aglycon units would greatly simplify the preparation of a wide variety of oligosaccharides, glycosides and glycoconjugates useful as i.a. synthetic biological receptors of the type described in Danish patent application No. 176/85 filed Jan. 14, 1985.

Recently, Lipshutz et al, *Tetrahedron Letters*, 1981, 22, p. 4603, reported the preparation of 2-trimethylsilylethyl glycosides and their subsequent cleavage by $LiBF_4$ to the corresponding free sugar using $LiBF_4$ or a 1:1 mixture of $LiF/BF_3.Et_2O$. However, Lipshutz does not indicate whether the cleavage product (or some intermediate) could have conserved its anomeric stereostructure.

SUMMARY OF THE INVENTION

Intensive studies by applicants have now indicated that the reagent used by Lipshutz (viz. $LiBF_4$) is not optimal in that it causes the reaction rate to be many times slower than what may be attained by the method according to the invention. Furthermore, his mechanistic interpretation is in contrast to the findings by applicants. Thus, using a 2-trimethylsilylethyl glycoside as a model system applicants have found that when using the reagent described by Lipshutz, the reaction was much slower than if LiF was deleted which means that $BF_3$ is the reactive species in a six-membered transition state as follows:

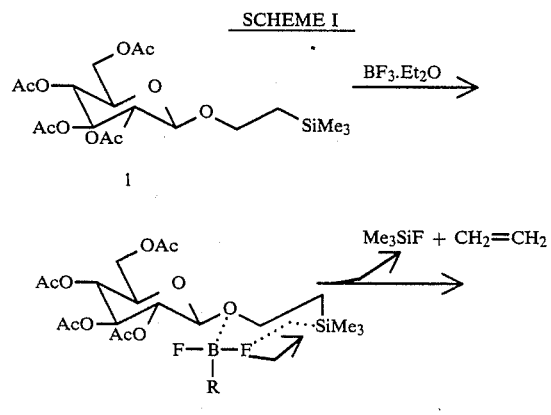

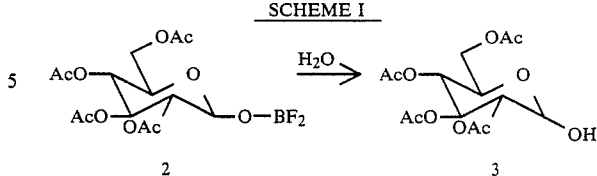

Consequently, in a first aspect, the present invention concerns a method for preparing an unprotected hydroxy compound from a protected hydroxy compound of the general formula I

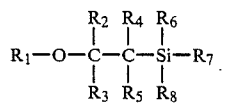

in which
$R_1$ is the non-hydroxy moiety of the protected hydroxy compound;
$R_2$, $R_3$, $R_4$ and $R_5$ which may be the same or different are hydrogen, $C_{1-4}$ alkyl or aryl;
and $R_6$, $R_7$ and $R_8$ which may be the same or different are $C_{1-4}$ alkyl, optionally substituted phenyl or a carrier
in which the compounds of formula I is reacted with a Lewis acid followed by reaction with water forming a hydroxy compound of the general formula II $$R_1-OH \qquad II$$

in which $R_1$ is as defined above.

The term "$C_{1-4}$ alkyl" designates a branched or straight chain alkyl group of up to 4 carbon atoms such as methyl, ethyl, propyl, isopropyl, butyl, isobutyl or tert.-butyl. The term "aryl" designates an aromatic group such as phenyl, which may be substituted with 1-3 identical or non-identical groups selected from halogen, e.g. fluoro, bromo or iodo, $C_{1-4}$ alkoxy, where the alkyl part is as defined above, $C_{1-4}$ alkoxy carbonyl, where the alkyl part is as defined above, or nitro. The term "optionally substituted phenyl" designates a phenyl group which may be substiuted with 1-3 substituents selected from those mentioned immediately above.

In the present context, the term "a carrier" for $R_6$, $R_7$ or $R_8$ designates any organic or inorganic, polymeric or macromolecular structure to which the silicon atom in the compound of the general formula I is attached. Examples of such carriers are residues of proteins, polysaccharides, inorganic materials and plastic polymers. Residues of proteins may be bound via groups in the proteins, such as amino, hydroxy and mercapto groups. The proteins themselves may be any of a wide variety of proteins, such as globulins, albumins, fibrins, polylysin etc. The polysaccharides, to which the silicon atoms are attached, may be any of a wide variety of polysaccharides such as cellulose, starch, glycogen, chitosane, sepharose or thio-modified polysaccharides. Examples of inorganic materials, to which the silicon atom may be attached, are silicon oxide materials such as silica gel, zeolite, diatomaceous earth or the surface of various functionalized glass or silica gel types where the silica gel or the glass may be in the form of e.g. beads. Another example of an inorganic material is aluminium oxide. A particularly important class of carrier are plastic polymers, in particular the various types of modified polystyren polymers generally used as support in polymer-supported synthesis, e.g. Merrifield-type polymers such as halogenmethylated polystyrenes, e.g. chloromethylated polystyrene.

With respect to the hydroxy compounds of which $R_1$ is the non-hydroxy moiety, i.e. the moiety to which the hydroxyl group is bound, such hydroxy compounds may be any of a wide variety of hydroxy compounds, such as hydroxy compounds having other protected groups in the molecule, e.g. protecting groups that are base-labile. Important examples of hydroxy compounds are hydroxy-containing amino acids such as serine or tyrosine or hydroxy-derivatives of other natural or synthetic amino acids, the amino acid optionaly forming part of a peptide. Another important class of hydroxy compounds are carbohydrates attached through the 1-carbon atom or derivatives thereof, in particular protected derivatives thereof.

Examples of important carbohydrate moieties are listed below. In the list, the various saccharide units are written according to the commonly use short-hand within the field in which the bonding between each saccharide unit (given as an abbreviation) is specified with respect to between which carbon atom in either saccharide unit the bond exists, and whether the bond is in an $\alpha$- or $\beta$-configuration. The designation "NAc" or "NPhth" means that the saccharide unit in question carries an acetylamino or a phthalimido group, respectively, in the 2-position. The simple "A" means the corresponding acid. Thus, "GlcA" is glucuronic acid. The notation "3Me" means that the hydroxy group normally present in the 3-position has been replaced by a methyl group. Analogously, "3CH$_2$OH" refers to a hydroxymethyl group. Although, the saccharides units may be present in both furanosidic and pyranosidic forms, pyranosidic units are normally preferred.

Examples of the carbohydrate moieties are:
Gal
Glc
Man
Fuc
Xyl
Rib
Ara
GlcNAc
GalNAc
GlcA
GalA
ManA
GlcNphth
GalNphth
NeuNAc
Man$\alpha$1-3Man
Man$\alpha$1-2Man
Man$\alpha$1-6Man
Man$\beta$1-4GlcNAc
Gal$\beta$1-4GlcNAc
GlcNAc$\beta$1-4Man
GlcNAc$\beta$1-2Man
Gal$\beta$1-6GlcNAc
Fuc$\alpha$1-6GlcNAc
Man$\alpha$1-6GlcNAc
Gal$\beta$1-2Man
Fuc$\alpha$1-3GlcNAc
Fuc$\alpha$1-2Gal
Fuc$\alpha$1-3Gal
Fuc$\alpha$1-6Gal
Gal$\beta$1-3GlcNAc
Gal$\beta$1-2Gal
Gal$\beta$1-6Gal
Gal$\beta$1-3Gal
GalNAc$\alpha$1-3Gal
GlcNAc$\beta$1-3Gal
Gal$\beta$1-4Glc
Gal$\alpha$1-4Gal
GalNAc$\beta$1-3Gal
GalNAc$\alpha$1-3GalNAc
GalNAc$\beta$1-4Gal
Gal$\beta$1-3GalNAc
Gal$\alpha$-3Gal
Glc$\alpha$1-6Glc$\alpha$1-4Glc$\alpha$1-4Glc
Glc$\alpha$1-4Glc
Glc$\beta$1-4Glc
NeuNAc$\alpha$2-3Gal
NeuNAc$\alpha$2-6Gal
NeuNAc$\alpha$2-3GalNAc
NeuNAc$\alpha$2-6GlcNAc
NeuNAc$\alpha$2-8NeuNAc
Glc$\beta$1-4Glc$\beta$1-4Glc
Glc$\alpha$1-4Glc$\alpha$1-4Glc
Man$\alpha$1-3(Man$\alpha$1-6)Man
Gal$\beta$1-3GalNAc$\beta$1-4Gal$\beta$1-4Glc
GalNAc$\beta$1-4Gal$\beta$1-3GalNAc$\beta$1-4Gal$\beta$1-4Glc
GalNAc$\beta$1-3Gal$\alpha$1-4Gal$\beta$1-4Glc
GalNAc$\beta$1-3Gal$\alpha$1-3Gal$\beta$1-4Glc
Gal$\beta$1-4GlcNAc$\beta$1-3Gal$\beta$1-4Glc
Gal$\beta$1-3GlcNAc$\beta$1-3Gal$\beta$1-4Glc
Gal$\beta$1-4GlcNAc$\beta$1-3Gal$\beta$1-4GlcNAc$\beta$1-3Gal$\beta$1-4Glc

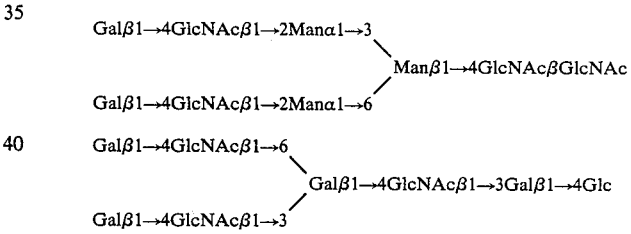

Gal$\beta$1-3Gal$\beta$1-4Glc
Gal$\beta$1-3Gal$\beta$1-3Gal$\beta$1-4Glc
GlcNAc$\beta$1-3Gal
Gal$\beta$1-4Glc3Me
Gal$\alpha$1-4Gal3Me
Gal$\beta$1-4Glc3CH$_2$OH
Gal$\alpha$1-4Gal3CH$_2$OH
Gal$\alpha$1-4Gal$\beta$1-4Glc
Gal$\alpha$1-4Gal$\beta$1-4GlcNAc
Glc$\alpha$1-6Glc$\alpha$1-4Glc It should be understood that the above list of carbohydrate moieties is by no means exhaustive but that the individual moieties listed may equally well represent internal or terminal fragments of higher saccharides.

In the above reaction, it is preferred, that $R_2$, $R_3$, $R_4$ and $R_5$ each are hydrogen, $R_6$, $R_7$ and $R_8$ are each preferably methyl.

The term "Lewis acid" designates any of the Lewis acids used in organic synthetic reactions. Lewis acids may generally be characterized in having an incompletely filled electron shell, the shell normally lacking two electrons. Examples of useful Lewis acids are BF$_3$, ZnCl$_2$, FeCl$_3$, MgBr$_2$, AlCl$_3$, SnCl$_4$, ZnBr$_2$, TiCl$_4$, TiF$_4$, BBr$_3$, SnBr$_4$ or TiBr$_4$. Examples of other potentially useful Lewis acids are LiF, LiCl, LiBr, LiBF$_4$, LiClO$_4$, MgCl$_2$, MgBr$_2$, MgI$_2$, MgF$_2$, MgO, CaF$_2$, CaCl$_2$, CaBr$_2$, CaI$_2$, TiI$_4$, TiO$_2$, CrO$_3$, CoCl$_2$, CoBr$_2$, CoI$_2$, NlCl$_2$, NiBr$_2$, NiI$_2$, CuCl$_2$, CuBr$_2$, CuI$_2$, AgCl, AgBr, AgI, Ag(OSO$_2$CF$_3$), ZnF$_2$, ZnI$_2$, CdCl$_2$, CdBr$_2$, CdI$_2$, HgCl$_2$, HgBr$_2$, HgI$_2$, Hg(CN)$_2$, HgSO$_4$, BCl$_3$, AlBr$_3$, AlI$_3$, C(C$_6$H$_5$)$_3$ClO$_4$, C(C$_6$H$_5$)$_3$CN, c(c$_6$H$_5$)$_3$BF$_4$, SiO$_2$, SnF$_4$, SnI$_4$, PCl$_3$, PBr$_3$, PF$_3$, SbF$_3$, SbCl$_3$, SbI$_3$, SbF$_5$, SbCl$_5$, AsF$_3$, (CH$_3$)$_3$OBF$_4$, and (CH$_3$CH$_2$)$_3$OBF$_4$.

The reaction may be carried out in a protic or aprotic, polar or apolar solvent examples of which are acetonitrile, nitromethane, ethyl acetate, ethers such as diethyl ether, halogenated hydrocarbons such as methylene chloride, chloroform or tetrachloromethane, aromatic hydrocarbons such as toluene or xylene, and lower alkanols such as methanol, ethanol or propanol. The reaction may be carried out at temperatures from 78° C. to 150° C., such as 0°–75° C., e.g. at room temperature for a period of from 1 minute to 3 days, such as 30 min. to 5 hours, e.g. 2 hours. The Lewis acid may be employed in an amount of 0.1–10 equivalents based on the protected hydroxy compound of the formula I, preferably 0.25–1 equivalent such as 0.8 equivalent.

In the article by Lipshutz (loc.cit), it was not stated whether the isolated products or some intermediates had retained the stereostructure of the starting material. If so, it would be theoretically possible to prepare acylated derivatives in stereospecific manner by including suitable acylating reagents in the reaction mixture. The instead of quenching the reaction mixture as in the method above (Scheme I), the presence of an acylating agent resulted in the stereospecific formation of an acylated form of the hydroxy compound of the general formula II as exemplified in Scheme II with a carbohydrate compound. The six-membered transition state indicated in Scheme II below explains the high obtainable degree of stereospecificity in the reaction.

SCHEME II

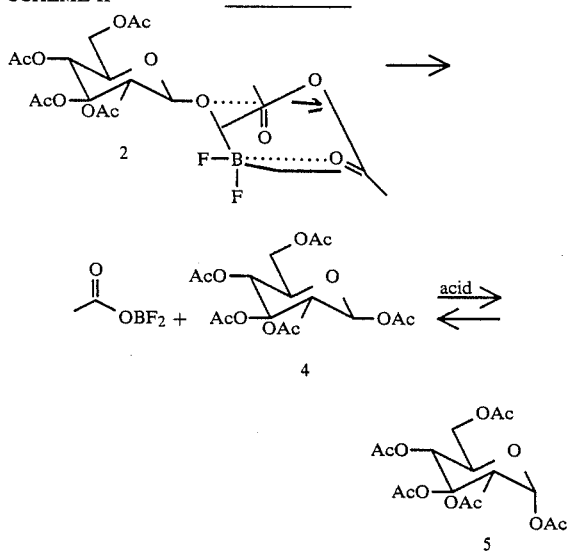

Consequently, in a second aspect, the present invention concerns a method for preparing a compound of the general formula III

—O—     III in which
R$_1$ is the non-hydroxy moiety of a hydroxy compound; and
A is an acyl group
comprising reacting a protected hydroxy compound of the formula I

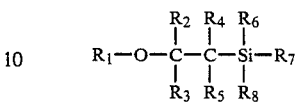

in which R$_1$, R$_2$, R$_3$, R$_4$, R$_5$, R$_6$, R$_7$ and R$_8$ are as defined above with a Lewis acid in the presence of the activated derivative of an acid of the general formula A—OH where A is as defined above.

R$_2$, R$_3$, R$_4$ and R$_5$ are preferably each hydrogen, R$_6$, R$_7$ and R$_8$ are peferably each methyl.

R$_1$ is preferably the non-hydroxy moiety of a hydroxy-containing amino acid, the amino acid optionally forming part of a peptide or is a carbohydrate moeity attached to the the oxygen atom through the 1-carbon atom or a derivative thereof.

As examples of Lewis acids may be mentioned the same as those given above.

The acid of formula A—OH of which an activated derivative is used, may be a carboxylic acid such as an optionally substituted C$_{1-25}$ alkanoic acid, an optionally substituted aryl-carboxylic acid or an optionally substituted heterocyclic-carboxylic acid; or may be the sulphonic acids corresponding to such carboxylic acids. Carboxylic acids are preferred.

The activated derivative of the acid is preferably an anhydride such as a symmetric or a mixed anhydride.

Examples of useful anhydrides are
Valeric anhydride
Dichlorofluoroacetic anhydride
Butyric anhydride
Isobutyric anhydride
Isovaleric anhydride
Trifluoroacetic anhydride
Acetic anhydride
Trimethylacetic anhydride
Dichloroacetic anhydride
Heptafluorobutyric anhydride
N-butyric anhydride
Nicotinic anhydride
Hexanoic anhydride
Heptanoic anhydride
Chloroacetic anhydride
Benzoic anhydride
Propionic anhydride
3-Methylcrotonic acid anhydride
Crotonic anhydride
Trichloroacetic anhydride
Oleic anhydride
p-Nitrobenzoic anhydride
2,4-Dinitrobenzoic anhydride
p-Methoxybenzoic anhydride
p-Trifluoroacetamidobenzoic anhydride
p-Nitrobenzoic-acetic anhydride
Stearic anhydride
Acetic-p-nitrobenzoic mixed anhydride.

The preparation of the compound of the formula III may be carried out in an aprotic, polar or apolar solvent, examples of which are acetonitrile, nitromethane, ethyl acetate, ethers such as diethyl ether, halogenated hydrocarbons such as methylene chloride, chloroform or tetrachloromethane, and aromatic hydrocarbons such as toluene or xylene, or mixtures thereof, preferably acetonitrile, toluene or methylene chloride or mixtures thereof. The reaction may be carried out at temperatures from 78° C. to 150° C. such as 0°-75° C., e.g. at room temperature for a period of from 1 minute to 3 days such as from 30 min. to 5 hours, e.g. 2 hours.

In a third aspect, the invention further concerns new intermediary compounds of the general formula IV $$R_1-O-X \qquad \text{IV}$$

in which $R_1$ is the non-hydroxy moiety of a hydroxy compound; and

X is a residue of a Lewis acid.

Such intermediary compounds are formed during the reaction preparing the compounds of the general formula III and may be isolated if the activated derivative of the acid of the formula A—OH is not present.

As mentioned above, $R_1$ is preferably the non-hydroxy moiety of a hydroxy-containing amino acid, the amino acid optionally forming part of a peptide, or is a carbohydrate moiety attached to the oxygen atom through the 1-carbon atom or a derivative thereof.

The residue of a Lewis acid may be the residue of any Lewis acid as defined above formed through the removal of one ligand atom. Examples of such residues are —BF$_2$, —ZnCl, —ZnBr, —FeCl$_2$, —MgCl, —MgBr, —AlCl$_2$, and —SnCl$_3$, —TiCl$_3$, —TiF$_3$, —BBr$_2$, —SnBr$_3$ or —TiBr$_3$.

In view of the above, a fourth aspect of the invention concerns a method for preparing a compound of the formula IV defined above comprising reacting a protected hydroxy compound of the formula I defined above with a Lewis acid under dry conditions.

The reaction for the preparation of a compound of the formula IV may be carried out in an aprotic, polar or apolar dried solvent, examples of which are acetonitrile, nitromethane, ethyl acetate, ethers such as diethyl ether, halogenated hydrocarbons such as methylene chloride, chloroform or tetrachloromethane, or aromatic hydrocarbons such as toluene or xylene, or mixtures thereof, preferably acetonitrile, methylene chloride or toluene or mixtures thereof. The reaction may be carried out at a temperature from —78° C. to 150° C. such as 0°-75° C., e.g. room temperature, for a period of from 1 minute to 3 days, such as from 30 min. to 5 hours, e.g. 2 hours.

An interesting class of compounds of the general formula I are compounds of the general formula Ia

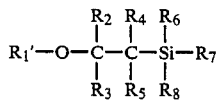

wherein $R_1'$ is a carbohydrate moiety containing two or more sugar units or a derivative thereof, and $R_2$, $R_3$, $R_4$, $R_5$, $R_6$, $R_7$ and $R_8$ are as defined above. Such compounds are useful in either the preparation of other glycosides of the carbohydrate moiety $R_1$, or the preparation of compounds having carbohydrate moieties with an increased number of sugar units in it.

Thus, a compound of the general formula Ia may be prepared by a method in which a compound of the general formula Ib

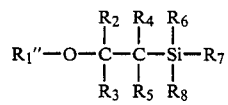

wherein $R_1''$ is a partially carbohydrate moiety containing one or more sugar units less than the group $R_1'$ in the formula Ia is subjected to a glycosidation reaction with a protected and activated sugar derivative and optionally followed by removal of the protective groups. Examples of activated sugar derivatives are 1-halogeno sugars such as 1-bromo sugars, 1-acyl sugars e.g. with acyl groups corresponding to the above-mentioned acid anhydrides, 1,2-orthoester sugars, 1,2-oxazolin sugars etc. Such a lengthening of the carbohydrate moiety to include more sugar units may also be carried out by enzymatic or microbial means such as reaction in the presence of carbohydrate-polymerizing enzymes or in the presence of microorganisms capable of generating oligosaccharides from shorter saccharide "building blocks". Of special interest is the use of glycosidases where the equilibrium between lower and higher saccharides can be shifted towards the higher saccharides by the use of organic solvents (e.g. dimethylformamide, dimethylsulfoxide, dioxane, ethylene and propylene glycol) either as such or as mixtures with water.

The reaction for the preparation of compounds of the general formula Ia from compounds of the formula Ib may be carried out under conditions used conventionally for glycosidations, such as in an aprotic, polar or apolar solvent examples of which are acetonitrile, nitromethane, ethyl acetate, ethers such as diethyl ether, halogenated hydrocarbons such as methylene chloride, chloroform or tetrachloromethane, and aromatic hydrocarbons such as toluene or xylene, or mixtures thereof, preferably acetonitrile, methylene chloride or toluene or mixtures thereof. The reaction may be carried out at temperatures from —78° C. to 150° C. such as 0°-75° C., e.g. room temperature for a period of from 30 minutes to 7 days such 15 hours. The sugar derivative with which the compound of the formula Ib is reacted is preferably a sugar derivative activated in the 1-position and furthermore a catalyst is generally used. The activated sugar derivative may be a 1-halogen sugar such as a 1-bromo sugar in which case the glycosidation is preferably carried out in the presence of a metal salt catalyst, e.g. a mercury or silver compound such as HgBr$_2$, Hg(CN)$_2$, HgO, Ag$_2$CO$_3$, Ag(OSO$_2$CF$_3$), Ag(CN)$_2$. The activated sugar derivative may also be a 1-acylated sugar such as a 1-acetyl or 1-(p-nitrobenzoyl) sugar in which case the glycosidation is preferably carried out in the presence of a Lewis acid such as those described above, e.g. BF$_3$, SnCl$_4$ or FeCl$_3$.

A further aspect of the present invention concerns carbohydrate derivatives containing one or more monosaccharide units and being acylated in the C-1 and C-2 positions of the reducing sugar unit, wherein the acyl-groups in the C-1 and the C-2 positions are different. It should be noted that there exist no generally useful methods in the litterature for the preparation of such acylated sugar derivatives. The acyl group in the C-2 position (as well as in the other non-anomeric positions of the sugar) as well as in the C-1 position may independently be chosen among acyl groups corresponding to the acid anhydrides listed above, provided, as already described, that they are different.

As described above, the present invention makes it possible to, for the first time, prepare acylated sugar derivatives in a general way where the anomeric and the nonanomeric acyl groups are different. This opens new possibilities for glycoside synthesis where the starting materials and the glycosylating reaction conditions can be "fine-tuned" by an optimal combination of anomeric acyl group, aglycon, and catalyst. More specifically, the leaving group properties of the anomeric acyl group but also the properties of the acyloxonium-acylate ion pair generally accepted as the active intermediate in such glycosidation reactions can be chosen so as to facilitate the formation of the desired glycoside.

Accordingly, yet another aspect of the invention concerns a method for preparing a compound of the general formula V $$R_{10}-Y \qquad V$$

in which $R_{10}$ is a carbohydrate moiety containing one or more sugar units and being attached to Y through the 1-carbon atom, and Y is an alcohol or thiol group by reacting a carbohydrate derivative containing one or more sugar units and which is acylated in the C-1 and C-2 positions of the reducing sugar unit, the acyl groups in the C-1 and C2 positions being different, with an alcohol or a thiol of the formula Y-H in the presence of a Lewis acid. The resulting compound of the formula V is a synthetic glycoside incorporating the group Y as the aglycon.

The Lewis acid used in the reaction may be chosen among those defined above.

The alcohol or thiol Y-H may be any alcohol or thiol whose group Y will be useful as the aglycon in a synthetic glycoside for use e.g. as synthetic biological receptors. An interesting class of such alcohols and thiols are partially protected sugars and compounds of the general formula H-X-R-R' wherein X is oxygen or sulphur, R is an optionally branched alkylene chain with up to 25 carbon atoms or aryl, e.g. phenyl, the alkylene chain optionally having one or more sulphur atoms inserted, and R' is H, F, Cl, Br, I, CHO, CH(OR")$_2$ wherein R" is $C_{1-4}$ alkyl, NO$_2$, NH$_2$, OH, SH, COOH, COOCH$_3$, COOCH$_2$CH$_3$, CONHNH$_2$, or CON$_3$.

Examples of specific alcohols or thiols Y-H are:
HO—CH$_2$—CH(CH$_2$Br)$_2$
HO$_{13}$—(CH$_2$)$_2$Br
HO—(CH$_2$)$_8$COOCH$_3$
HO—(CH$_2$)$_2$—S—(CH$_2$)$_2$COOCH$_3$
HO—(CH$_2$)$_2$—S—(CH$_2$)$_{17}$CH$_3$
HO—CH$_2$—CH(CH$_2$—S—(CH$_2$)$_{15}$CH$_3$)$_2$
HO—CH$_2$-CH(CH$_2$—S—(CH$_2$)$_{10}$COOCH$_3$)CH$_2$—S—(CH$_2$)$_7$—CH$_3$
HS—(CH$_2$)$_2$COOCH$_3$
HS—(CH$_2$)$_{10}$COOCH$_3$
HS—C$_6$H$_5$
HS—C$_6$H$_4$NO$_2$
HS—C$_6$H$_4$NHCOCF$_3$
HO—CH$_2$C$_6$H$_5$
HO—C$_6$H$_4$NO$_2$
HO—C$_6$H$_4$NHCOCF$_3$
HO—CH$_3$
HO—CH$_2$CH$_3$
HO—CH(CH$_2$Br)$_2$ The reaction for the preparation of compounds of the formula V may be carried out in an aprotic polar or apolar solvent examples of which are acetonitril, nitromethane, ethyl acetate, ethers such as diethyl ether, halogenated hydrocarbons such as methylene chloride, chloroform or tetrachloromethane, or aromatic hydrocarbons such as toluene or xylene, or mixtures thereof. The reaction may be carried out at temperatures from −78° C. to 150° C. such as 0°–75° C., e.g. at room temperature, for a period of from 15 minutes to 3 days such as 15 hours.

The invention is further illustrated by the following non-limiting examples.

In the examples, the following general methods were used:

GENERAL METHOD FOR THE CLEAVAGE OF 2-TRIMETHYLSILYLETHYL GLYCOSIDES (EXAMPLES 1A–1I)

0.11 mmol of the glycoside starting material listed in Table I below was dissolved in 0.6 ml of the solvent listed. The listed reagents were added and the mixture was stirred at the temperature and for the time indicated. Addition of water, extraction with methylene chloride and removal of the solvents and optional purification by chromatography gave the product indicated.

GENERAL METHOD FOR THE STEREOSELECTIVE PREPARATION OF SUGAR 1,2-TRANS ACYLATES DIRECTLY FROM THE 2-TRIMETHYLSILYLETHYL GLYCOSIDES (EXAMPLES 2–47)

0.11 mmol of the glycoside starting material was dissolved in 0.6 ml of the solvent listed, and the reagents were added. The mixture was stirred at the temperature and for the time listed. The reaction products were checked with thin layer chromatography (TLC). For recovery of the product(s), 5 ml CH$_2$Cl$_2$ was added, and the solution was washed with 5% sodium bicarbonate solution and water, dried over MgSO$_4$ and filtered through silica to give the pure acylates after removal of the solvent. The $\alpha/\beta$ ratio was determined by gas chromatography or $^1$H-NMR spectroscopy.

Thin layer chromatography was carried out using Merck DC-Alufolien Kieselgel 60, F$_{254}$, 0.2 mm. The plates were developed with mixtures of ethyl acetate and hexane.

Gas chromatographical analysis (GC) was carried out on a column of RSL-300 50% polyphenyl-methylsiloxane (length 10 m, diameter 0.32 mm), 0.9 ml He/min, injector temperature 300° C., detector temperature 300° C.

$^1$NMR spectroscopy was carried out at 300 MHz in CDCl$_3$+0.1% TMS.

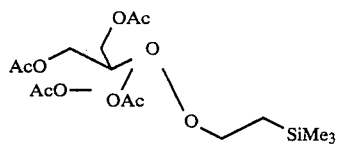 1
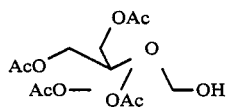 3
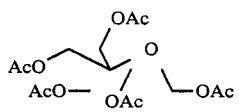 4
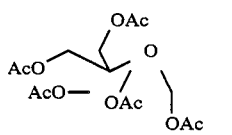 5
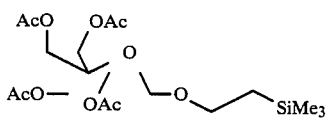 6
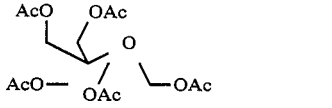 7
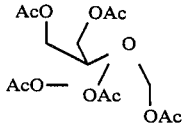 8
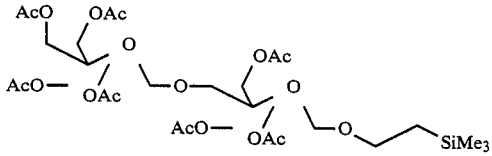 9
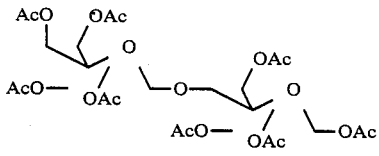 10
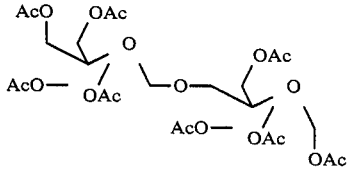 11

-continued
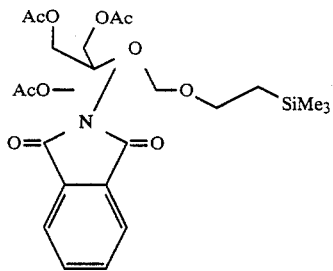 12
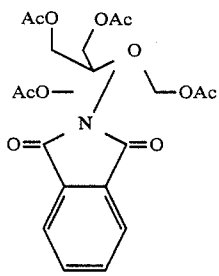 13
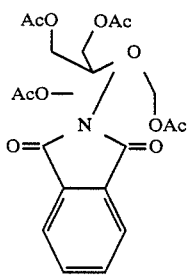 14
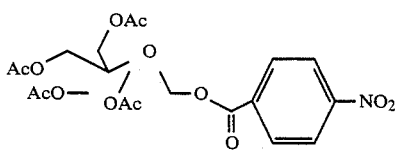 15
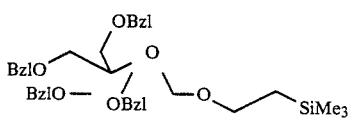 16
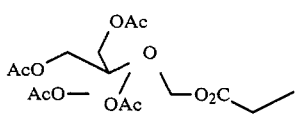 17
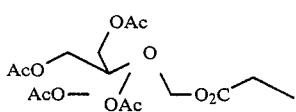 18
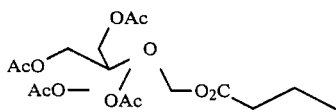 19
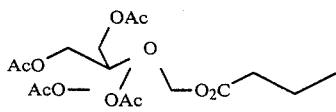 20

-continued
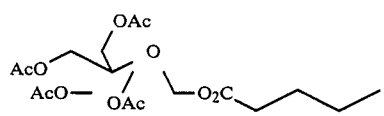  21
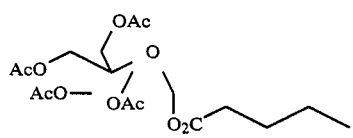  22
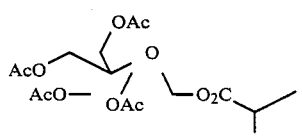  23
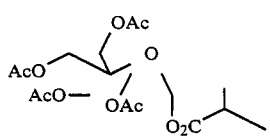  24
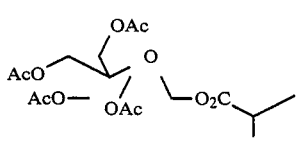  25
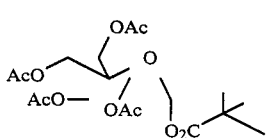  26
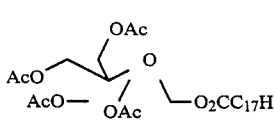  27
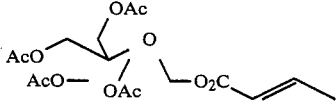  28
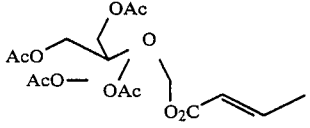  29
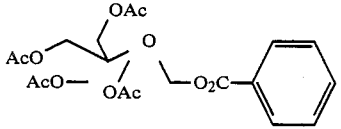  30
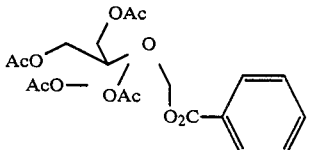  31
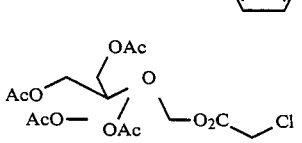  32

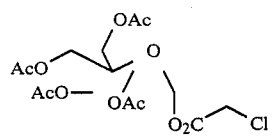 33
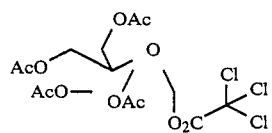 34
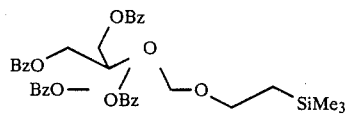 35
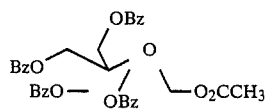 36
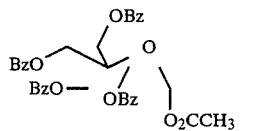 37
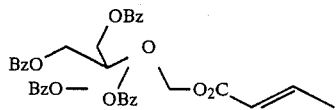 38
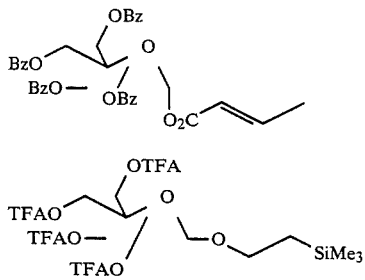 39
40
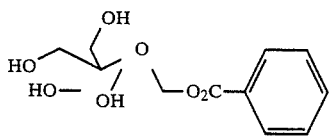 41
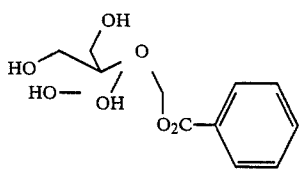 42
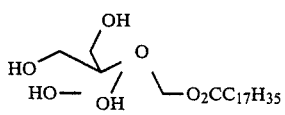 43
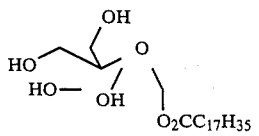 44

-continued

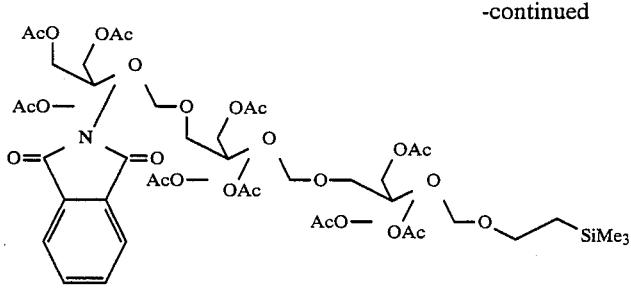   45

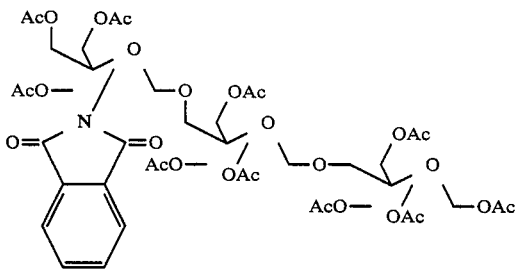   46

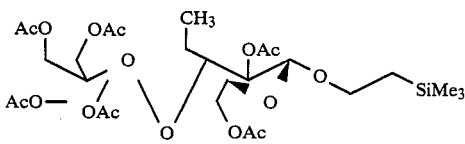   47

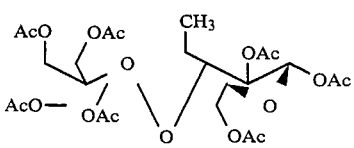   48

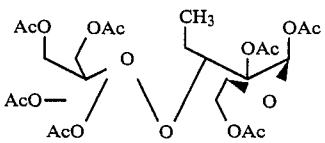   49

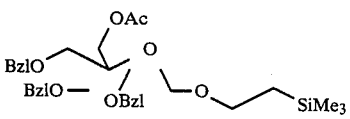   50

TABLE I

| EXAMPLE | STARTING MATERIAL | REAGENT | REACTION CONDITION | PRODUCT | YIELD % | β/α RATIO |
|---|---|---|---|---|---|---|
| 1A | 1 | LiBF$_4$ 10 eq | CH$_3$CN, 70° C., 17 hours | 3 | 95%[1] | |
| 1B | 1 | LiBF$_4$ 10 eq, 1 eq TFAA | CH$_3$CN, 70° C., 2 hours | 3 | 90%[1] | |
| 1C | 1 | LiBF$_4$ 10 eq, 2 eq TFA | CH$_3$CN, 50° C., 10 hours | 3 | 95%[1] | |
| 1D | 1 | NaF 10 eq + BF$_3$.Et$_2$O 9 eq | CH$_3$CN, 50° C., 1.5 hours | 3 | 95°[1] | |
| 1E | 1 | NaF 7 eq + BF$_3$.Et$_2$O 6 eq added to the stirred solution of NaF | CH$_3$CN, 50° C., | | no reaction | |
| 1F | 1 | BF$_3$.Et$_2$O 0.9 eq | CH$_3$CN, 20° C., 50 min. | 3 | 87%[3] | |
| 1G | 1 | BF$_3$.Et$_2$O 0.9 eq | CH$_3$CN, 20° C., 25 min. | 3 | 95%[1] | |
| 1H | 1 | BF$_3$.Et$_2$O 1 eq, succinic anhydride, 10 eq | CH$_3$CN, 20° C., 1 hour | 3 | 95% | |
| 1I | 1 | LiF 0.9 eq + BF$_3$.Et$_2$O 0.9 eq added to the stirred solution of LiF | CH$_3$CN, 20° C., 25 min. | 3 | 10%[1] | |
| 2 | 1 | BF$_3$.Et$_2$O 1 eq, p-nitrobenzoic anhydride 10 eq | CH$_3$CN, 20° C., 1 hour | 15 | 90%[1] | mixture |
| 3 | 1 | LiBF$_4$ 10 eq | CH$_3$CN, 70° C., 20 hours the addition of Ac$_2$O | 4/5 | 88%[2] | 40/60 (GC) |
| 4 | 1 | LiBF$_4$ 10 eq, TFAA 2 eq, Ac$_2$O 30 eq | CH$_3$CN, 20° C., 8 days | 4/5 | 90%[1] | 79/21 (GC) |

TABLE I-continued

| EXAMPLE | STARTING MATERIAL | REAGENT | REACTION CONDITION | PRODUCT | YIELD % | β/α RATIO |
|---|---|---|---|---|---|---|
| 5 | 1 | BF$_3$.Et$_2$O 0.5 eq | Ac$_2$O, 20° C., 48 hours | 4/5 | 87%[2] | 95/5 (GC) |
| 6 | 1 | FoCl$_3$/SiO$_2$ 0.5 eq | Ac$_2$O, 20° C., 50 min. | 4/5 | 95%[1] | 16/84 (GC) |
| 7 | 1 | BF$_3$.Et$_2$O 0.9 eq | Ac$_2$O, 20° C., 10 min. | 4/5 | 88%[2] | 89/11 (GC) |
| 8 | 1 | FeCl$_3$/SiO$_2$ 0.9 eq | Ac$_2$O, 20° C., 10 min. | 4/5 | 95%[1] | 18/82 (GC) |
| 9 | 1 | ZnCl$_2$ 0.9 eq added as solid | Ac$_2$O, 20° C., 3 days | 4/5 | 95%[1] | 15/85 (GC) |
| 10 | 1 | ZnCl$_2$ Sol.in Ac$_2$O 0.9 eq | Ac$_2$O, 20° C., 8 hours | 4/5 | 81%[2] | 86/14 (GC) |
| 11 | 1 | FeCl$_3$ Sol.in Ac$_2$O 0.9 eq | Ac$_2$O, 20° C., 20 min. | 4/5 | 95%[1] | 22/78 (GC) |
| 12 | 1 | SnCl$_4$ Sol.in Ac$_2$O 0.9 eq | Ac$_2$O, 20° C., 10 min. | 4/5 | 95%[1] | 60/40 (GC) |
| 13 | 1 | ZnBr$_2$ 0.9 eq added as solid | Ac$_2$O, 20° C., 24 hours | 4/5 | 90%[1] | 84/16 (GC) |
| 14 | 1 | 0.8 eq BF$_3$.Et$_2$O | 15 eq Ac$_2$O, 20° C., toluen 5 ml/mmol of sugar, 2 hours | 4/5 | 95% | 97/3 (GC) |
| 15 | 1 | 0.8 eq BF$_3$.Et$_2$O | 15 eq Ac$_2$O, 20° C., CH$_2$Cl$_2$ 5 ml/mmol, 2 hours | 4/5 | 80% | |
| 16 | 1 | 0.8 eq BF$_3$.Et$_2$O | 15 eq Ac$_2$O, 20° C., toluen 5ml/mmol 1 hour 50 min. | 4/5 mp 130-130.5 | 93%[3] | 99/1 (GC) |
| 17 | 6 | BF$_3$.Et$_2$O 0.9 eq | Ac$_2$O, 20° C., 50 min. | 7/8 | 85%[2] | 74/26 (GC) |
| 18 | 6 | BF$_3$.Et$_2$O 0.8 eq | 15 Ac$_2$O, 20° C., toluen 5 ml/mmol, 1 hour 50 min. | 7/8 | 92%[3] | 96/4 (GC) |
| 19 | 12 | BF$_3$.Et$_2$O 0.9 eq | Ac$_2$O, 20° C., 1.5 hour | 13/14 | 95%[2] | 80/20 (NMR) |
| 20 | 12 | BF$_3$.Et$_2$O 0.8 eq | 15 eq Ac$_2$O, 20° C., toluen 5 ml/mmol, 3 hours | 13/14 | 93%[3] | 97/3 (NMR) |
| 21 | 9 | BF$_3$.Et$_2$O 0.9 eq | Ac$_2$O, 20° C., 40 min. | 10/11 | 72%[2] | 89/11 (NMR) |
| 22 | 9 | FeCl$_3$/silica 0.9 eq | Ac$_2$O, 20° C., 40 min. | 10/11 | 85%[1] | |
| 23 | 9 | ZnCl$_2$ 1 eq added as solid | Ac$_2$O, 20° C., 15 hours | 10/11 | 85%[1] | |
| 24 | 9 | BF$_3$.Et$_2$O 0.8 eq | 15 eq Ac$_2$O, 20° C., toluen 5 ml/mmol, 3.5 hours | 10/11 | 95%[3] | 98/2 (NMR) |
| 25 | 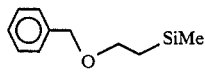 | BF$_3$.Et$_2$O 1 eq | CH$_3$CN, 20° C., 2 hours | 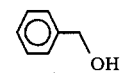 | >90% | |
| 26 | 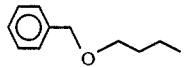 | BF$_3$.Et$_2$O 1 eq | CH$_3$CN, 20° C., 15 hours | no reaction | | |
| 27 | 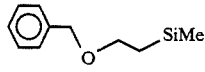 | BF$_3$.Et$_2$O 1 eq | Ac$_2$O, 20° C., 2 hours | 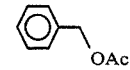 | >80% | |
| 28 | 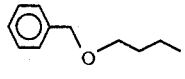 | BF$_3$.Et$_2$O 1 eq | Ac$_2$O, 20° C., 15 hours | 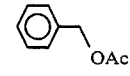 | >80% | |
| 29 | 1 | BF$_3$.Et$_2$O 0.7 eq | 1.1 eq Ac$_2$O, 60° C., 1 hour, toluene | 4/5 | 98% | 97/3 (GC) |
| 30 | 1 | BF$_3$.Et$_2$O 0.7 eq | 1.1 eq propionic anhydride, toluene, 60° C., 2 hours | 17/18 | 96% | 98/2 (GC) |
| 31 | 1 | BF$_3$.Et$_2$O 0.7 eq | 1.1 eq butyric anhydride, toluene, 60° C., 2 hours | 19/20 | 99% | 98/2 (GC) |
| 32 | 1 | BF$_3$.Et$_2$O 0.7 eq | 1.1 eq valeric anhydride, toluene, 60° C., 2 hours | 21/22 | 98% | 97/3 (GC) |
| 33 | 1 | BF$_3$.Et$_2$O 0.7 eq | 1.1 eq isobutyric anhydride, toluene, 60° C., 3 hours | 23/24 | 98% | 99/1 (GC) |
| 34 | 1 | BF$_3$.Et$_2$O 0.8 eq | 3 eq pivalic anhydride, 60° C., 9 hours | 25/26 | 98% | 97/3 (GC) |
| 35 | 1 | BF$_3$.Et$_2$O 0.7 eq | 1.1 eq stearic anhydride, toluene, 60° C., 2 hours, no extraction | 27 | 96% | 100/0.(MNR) |
| 36 | 1 | BF$_3$.Et$_2$O 0.8 eq | 1.5 eq crotonic anhydride, toluene, 60° C., 1 hour | 28/29 | 94% | 94/6 (GC) |
| 37 | 1 | BF$_3$. Et$_2$O 0.8 eq | 1.5 eq benzoic anhydride, toluene, 60° C., 6 hours | 30/31 | 98% | 94/6 (GC) |
| 38 | 1 | BF$_3$.Et$_2$O 0.8 eq | 3 eq monochloroacetic anh., toluene, 60° C., 1 hour | 32/33 | 87% | 58/42 (GC) |
| 39 | 1 | BF$_3$.Et$_2$O 0.8 eq | 10 eq trichloroacetic anh., toluene, 60° C., 2 hours no chromatography | 34 | 80% | 0/100 (NMR) |
| 40 | 1 | BF$_3$.Et$_2$O 0.8 eq | 1.5 eq H$_3$COOCO(p-NO$_2$—O) mp 77-80°, toluene, 60° C. 1 hour | 4/5 15 | 21% 77% | 95/5 (GC) 100/0 (NMR) |
| 41 | 35 | BF$_3$.Et$_2$O 0.7 eq | 1.1 eq acetic anhydride, toluene, 60° C., 1 hour | 36/37 | 96% | 100/0 (NMR) |

TABLE I-continued

| EXAMPLE | STARTING MATERIAL | REAGENT | REACTION CONDITION | PRODUCT | YIELD % | β/α RATIO |
|---|---|---|---|---|---|---|
| 42 | 35 | BF$_3$.Et$_2$O 0.8 eq | 1.5 eq crotonic anhydride, toluene, 60° C., 1 hour | 38/39 | 97% | 100/0 (NMR) |
| 43 | 16 | BF$_3$.Et$_2$O 0.5 eq | acetic anhydride, 25° C., 0.5 hours | 50 | 37% | |
| 44 | 40 | BF$_3$.Et$_2$O 0.8 eq | 2.0 eq benzoic anhydride, toluene, 55° C., 3 hours then MeOH | 41/42 | 79% (Cryst. from MeOH gave 35% pure β anomer) | 70/30 (NMR) |
| 45 | 40 | BF$_3$.Et$_2$O 0.8 eq | 1.2 eq stearic anhydride, toluene, 55° C., 3 hours then MeOH | 43/44 | 71% (Cryst. from MeOH gave 35% pure β anomer) | |
| 46 | 45 | BF$_3$.Et$_2$O 0.7 eq | 1.1 eq acetic anhydride, toluene, 60° C., 2 hours | 46 | 91% | 100/0 (NMR) |
| 47 | 47 | BF$_3$.Et$_2$O 0.8 eq | 1.5 eq acetic anhydride, toluene, 60° C., 0.5 hours | 48/49 | 90% | 30/70 (NMR) |

[1]According to TLC
[2]Yield after chromatography
[3]Extraction with CH$_2$Cl$_2$
TFA = Trifluoroacetic acid or trifluoro acetyl
TFAA = Trifluoroacetic anhydride
Bz = Benzoyl
Bzl = Benzyl

TABLE 2

| | Selected Physical - and Spectral Data. | | |
|---|---|---|---|
| Compound No. | Mp (°C.) | [α]$_D^\circ$ (c = 1 CHCl$_3$) | $^1$H—Nmr (CDCl$_3$, Me$_4$Si) δ/J (ppm/Hz) anomeric H |
| 1 | 65–67 | −22.0 | 4.51/7.80 |
| 3β | — | — | 4.75/7.81 |
| 3α | — | — | 5.47/3.67 |
| 4 | 131–132 | 4.8 | 5.72/8.55 |
| 6 | — | −14.0 | 4.48/7.80 |
| 9 | — | −16.5 | 4.48/7.8; 4.47/7.8 |
| 10 | — | — | 5.67/8.30 |
| 11 | — | — | 6.25 |
| 12 | — | −9.9 | 5.34/8.60 |
| 13 | — | — | 6.45/9.28 |
| 14 | — | — | 6.34/3.18 |
| 15 | 223–225 | −33.2 | 5.93/virtual coupling |
| 17 | 97–98 | 4.8 | 5.73/7.92 |
| 19 | 81–82 | 3.5 | 5.74/7.82 |
| 21 | 61–62 | 1.8 | 5.72/8.30 |
| 23 | 111–112 | 4.6 | 5.73/8.06 |
| 25 | 135–136 | 7.3 | 5.68/7.81 |
| 27 | 77–78 | 1.3 | 5.72/8.54 |
| 28 | 93–95 | −7.3 | 5.78/8.06 |
| 30 | 144–145 | −25.9 | 5.93/virtual coupling |
| 32/33 (β58/α42) | 107–108 | 34.3 | β: 5.78/8.55; α: 6.4/3.66 |
| 34 | 124–127 | 96.5 | 6.44/3.66 |
| 35 | — | 17.9 | 4.88/7.81 |
| 36 | 189–191 | 57.7 | 6.10/7.82 |
| 38 | — | 43.1 | 6.14/7.82 |
| 40 | — | 3.2 | 4.73/7.81 |
| 41 | 185–190 | −2.6 (dioxan) | 5.75/7.81 (CDCl$_3$: MeOD) |
| 42 | — | — | 6.38/3.66 (CDCl$_3$: MeOD) |
| 43 | 108–111 | 1.2 (dioxan) | 5.33/8.55 (DMSO) |
| 45 | — | — | 4.43/7.81; 4.29/7.92; 5.25/8.71 |
| 46 | — | — | 5.63/8.05; 4.29/7.56; 5.26/8.30 |
| 47 | — | −59.0 | 5.09/3.70; 4.38/7.90 |
| 48 | — | — | 5.63/8.08; 5.13/3.80 |
| 49 | — | — | 6.28/3.30; 5.10/3.20 |
| 50 | — | — | 4.40/7.80 |

SYNTHESIS OF STARTING MATERIALS 1, 6 AND 9

The relevant acetobromosugar (1 equiv.), HgO (1 eq.), a catalytic amount of HgBr$_2$, CaSO$_4$ (2 eq.) and 2-trimethylsilylethanol (1.5 eq.) was dissolved in sufficient dry CHCl$_3$ to give a 0.33M solution of the acetobromosugar. The mixture was stirred at room temperature until the acetobromosugar had been consumed (checked by TLC) and worked up by partitioning between water and CH$_2$Cl$_2$. The organic phase was dried over Na$_2$SO$_4$, concentrated, and the residue was chromatographed (SiO$_2$, ethyl acetate/heptane) to give the pure product. Physical data of the products are given below.

COMPOUND 1

2-Trimethylsilylethyl 2,3,4,6-tetra-O-acetyl-β-D-glucopyranoside $^1$H-NMR δ(ppm)=5.20 (t, 1H, J$_{32}$=J$_{34}$=9.6, H3), 5.09 (t, 1H, J$_{43}$=J$_{45}$=9.6, H4), 4.97 (dd, 1H, J$_{23}$=9.6 J$_{21}$=7.8, H2), 4.51 (d, 1H, J$_{12}$=7.8, H1), 4.26 4.13 (d of ABq, 2H, J$_{AB}$=12 J$_{65}$=4.8 J$_{65}$=2.7, H6), 3.97 3.56 (q of ABq, 2H, $J_{AB}=10.5$ $J_{AC}=9.6$ $J_{AD}=5.7$ $J_{BC}=6.9$ $J_{BD}=10.5$ —O—CH$_2$—), 3.69 (q of d, 1H, $J_{54}=9.6$ $J_{56}=4.8$ $J_{56}=2.7$, H5), 2.08 2.04 2.02 2.00 (four singlets, 12H, —OCOCH$_3$), 0.96 0.90 (q of CD$_q$, 2H, $J_{CD}=14$ $J_{CA}=9.6$ $J_{CB}=6.9$ $J_{DA}=5.7$ $J_{DB}=10.5$, —CH$_2$—SiMe$_3$), 0.01 (S, 9H, SiMe$_3$).

$[\alpha]_D^{25} = -19°$ (c=1 CHCl$_3$).

COMPOUND 6

2-trimethylsilylethyl 2,3,4,6-tetra-O-acetyl-β-D-galactopyranoside $^1$H-NMR δ(ppm)=5.39 (dd, 1H, $J_{43}=3.3$ $J_{45}=1.0$, H4), 5.20 (dd, 1H, $J_{21}=7.8$ $J_{23}=10.5$, H2), 5.10 (dd, 1H, $J_{32}=10.5$ $J_{34}=3.3$, H3), 4.48 (d, 1H, $J_{12}=7.8$, H1), 4.20 4.13 (d of ABq, 2H, $J_{AB}=11.4$ $J_{65}=6.6$, H6), 3.99 3.57 (q of ABq, 2H, $J_{AB}$ 10.5 $J_{AC}$32 5.7 $J_{AD}=9.6$ $J_{BC}=10.5$ $J_{BD}=6.9$, —O—CH$_2$—), 3.90 (dt, 1H, $J_{56}=6.6$ $J_{54}=1.0$, H5), 2.15 2.05 2.05 1.98 (four singlets, 12H —OCOCH$_3$), 0.98 0.92 (q of CDq, 2H, $J_{CD}=14$ $J_{DB}=6.9$ $J_{DA}=9.6$ $J_{CB}=10.5$ $J_{CA}$ 5.7, —CH$_2$—SiMe$_3$), 0.01 (S 9H, SiMe$_3$).

$[\alpha]_D^{25} = -14.0°$ (c=1 CHCl$_3$).

COMPOUND 9

2-trimethylsilylethyl 2,3,6-tri-O-acetyl-4-O-(2,3,4,6-tetra-O-acetyl-β-D-galactopyranosyl)β-D-glucopyranoside $^1$H-NMR δ(ppm)=5.35 (dd, 1H, $J_{4'5'}=1$ $J_{4'3'}=3.4$, H4'), 5.19 (t, 1H, $J_{32}=9.3$ $J_{34}=9.3$, H3), 5.11 (dd, 1H, $J_{2'3'}=10.5$ $J_{2'1'}=7.81$, H2'), 4.95 (dd, 1H, $J_{3'2'}=10.5$ $J_{3'4'}=3.4$, H3'), 4.88 (dd, 1H, $J_{23}=9.5$ $J_{21}=7.81$, H2), 4.48 4.47 (two doublets, J=7.81, H1 and H1'), 4.10 (m, 2H, H6, H6'), 3.94 3.55 (q of ABq, 2H, $J_{AB}=10.5$ $J_{AC}=10$ $J_{AD}=5.8$ $J_{BC}=6.9$ $J_{BD}=10.0$, —OCH$_2$—), 3.87 (dt, 1H, $J_{5'6'}=7.6$ $J_{5'4'}=1$, H5'), 3.79 (t, 1H, $J_{43}=9.8$ $J_{45}=9.8$, H4), 3.60 (q of d, 1H, $J_{54}=9.8$ $J_{56}=5.1$ $J_{56}=2$, H5), 2.15 2.11 2.06 2.05 2.04 2.03 1.97 (seven singlets 21H, COCH$_3$), 0.93 0.90 (q of CDq, 2H, $J_{CD}=14$ $J_{CA}=10.0$ $J_{CB}=6.9$ $J_{DA}=5.8$ $J_{DB}=10.0$, —CH$_2$—SiMe$_3$), 0.0 (S, 9H, —SiMe$_3$).

$[\alpha]_D^{25} = -16.5°$ (c=1 CHCl$_3$).

SYNTHESIS OF STARTING MATERIAL 12

2-Trimethylsilylethanol (1.5 eq.), Ag(OSO$_2$CF$_3$) (1.5 eq.) and 2,4,6-trimethylpyridine (1.5 eq.) was dissolved in sufficient nitromethane to give a 0.5M solution of the silylethanol. 1-Bromo-2-deoxy-2-phthalimido-3,4,6-tri-O-acetyl-α-D-galactopyranose (1 eq.) was dissolved in nitromethane and added to the above mixture at −20° C. After 2 hours, the mixture was allowed to warm up to room temperature and worked up as for the previous starting materials above giving the pure product. Physical data are given below.

COMPOUND 12

2-trimethylsilylethyl 2-deoxy-2-phthalimido-3,4,6-tri-O-acetyl-β-D-galactopyranoside $^1$H-NMR δ(ppm)=7.86 7.75 (two q, 4H, φ), 5.78 (dd, 1H, $J_{34}=3.6$ $J_{32}$11.4, H3), 5.48 (dd, 1H, $J_{43}=3.6$ $J_{45}=1.0$, H4), 5.34 (d, 1H, $J_{12}=8.6$, H1), 4.54 (dd, 1H, $J_{21}=8.6$ $J_{23}=11.4$, H2), 4.25 4.19 (d of ABq, 2H, $J_{AB}=11.2$ $J_{65}=7.1$, H6), 4.08 (dd, 1H, $J_{54}=1.0$ $J_{56}=7.1$, H5), 3.95 3.53 (q of ABq, 2H, $J_{AB}=11.0$ $J_{AC}=5.6$ $J_{AD}=9.8$ $J_{BC}=10.0$ $J_{BC}=10.0$ $J_{BD}=6.8$, —O—CH$_2$—), 2.20 2.07 1.85 (3S, 9H, —OCOCH$_3$), 0.85 0.76 (q of CDq, 2H, $J_{CD}$ 14 $J_{CA}$ 5.6 $J_{CB}$ 10.0 $J_{DA}=9.8$ $J_{DB}=6.8$, —CH$_2$—SiMe$_3$), −0.01 (S, 9H, SiMe$_3$).

$[\alpha]_D^{25} = -9.9°$ (c=1 CHCl$_3$).

Synthesis of starting material 16

2-Trimethylsilylethyl 2,3,4,6-tetra-O-benzyl-β-D-glucopyranoside

Compound 1 (0.5 g, 1.11 mmol) was dissolved in methanol (5 mL) and methanolic sodium methoxide (50 μL, 0.5M) was added. The mixture was stirred for 1.5 h, neutralised by the addition of acetic acid and the solvent was removed. Benzyl chloride (2.4 mL) and potassium hydroxide (1 g) were added, the mixture was stirred overnight at 130° and then partitioned between dichloromethane and water. Separation of the organic phase, drying (Na$_2$SO$_4$) and removal of the solvent gave crude 16. Chromatography (SiO$_2$, hexane/ethyl acetate 12:1) gave pure 16 (0.61 g, 86%).

SYNTHESIS OF STARTING MATERIAL 35

2-Trimethylsilylethyl 2,3,4,6-tetra-O-benzoyl-β-D-glucopyranoside

Compound 1 was deacetylated as above and the product (1 g) was dissolved in pyridine (10 mL) and benzoyl chloride (2 equivalents) was added. After 12 h at room temperature, water (1 mL) was added and the mixture was stirred for 15 min. Dichloromethane was added and the mixture was washed consequtively with water, hydrochloric acid (1M) and water. The organic phase was dried (Na$_2$SO$_4$), the solvent was removed and the residue was submitted to chromatography (SiO$_2$, hexane/ethyl acetate 3:1) to give pure 35 as a sirup (1.95 g, 78%).

SYNTHESIS OF STARTING MATERIAL 40

2-Trimethylsilylethyl 2,3,4,6-tetra-O-trifluoroacetyl-β-D-glucopyranoside

Compound 1 was deacetylated as above and the product was crystallised from ethyl acetate. The product (1.02 g, 3.65 mmol) and sodium trifluoroacetate (0.27 g, 1.94 mmol) were heated in an oil-bath (50°) and trifluoroacetic anhydride (5.9 mL, 42 mmol) was added. After reflux for 25 min, the oil bath was removed and residual trifluoroacetic acid was coevaporated with three portions of tetrachloromethane. The residue was extracted with hot dichloromethane followed by removal of the solvent, which gave crude 40 (2.40 g) for immediate use in the synthesis of 41, 42, 43 and 44.

SYNTHESIS OF COMPOUNDS 41, 42, 43 AND 44

1-O-benzoyl-β-D-glucopyranoside,
1-O-benzoyl-α-D-glucopyranoside,
1-O-stearoyl-β-D-glucopyranoside,
1-O-stearoyl-α-D-glucopyranoside Compound 40 (2.37 g, 3.57 mmol) and benzoic anhydride (2 equiv.) or stearic anhydride (1.2 equiv.) were dissolved in toluene (5 mL/mmol of 40) and borontrifluoride etherate (0.8 or 0.7 equiv., respectively) was added. The mixture was stirred at 55° C. for 3 or 5 h, respectively and then poured into methanolic sodium hydrogencarbonate (14 mL/mmol of 40). After stirring for 15 min, the solvent was removed and the residue was extracted with chloroform/methanol 9.1. The volume of the extract was reduced and concentrated solution was submitted to chromatography (SiO$_2$, CHCl$_3$/MeOH, 4:1) or EtOAc/MeOH, 20:1, respectively). Crystallisation from methanol gave the products 41/42 or 43/44, respectively (see Table 1 and 2).

SYNTHESIS OF STARTING MATERIAL 45

2-Trimethylsilylethyl 2,3,6-tri-O-acetyl-4-O-[2,3,6-tri-O-acetyl-4-O-(3,4,6-tri-O-acetyl-2-deoxy-2-phthalimido-β-D-galactopyranosyl)-β-D-galactopyranosyl]-β-D-glucopyranoside Compound 9 was conventionally deacetylated and the product was 4,6-O-benzylidenated, then benzylated with benzyl bromide/sodium hydride/dimethyl formamide. The 4,6-O-benzylidene protecting group was reductively opened to give a derivative that was used as aglycon in the glycosidation with tri-O-acetyl-2-deoxy-2-phthalimido-α,β-D-galactopyranosyl bromide. Hydrogenolytic removal of the benzyl groups and acetylation with acetic anhydride/pyridine gave crude 45. Chromatography (SiO₂, CH₂Cl₂/heptane/EtOAc, 1:1:2) then gave the pure compound. The over-all synthesis (9–45) was performed in 13% yield, essentially as described (S. Sabesan, R. U. Lemieux, Can. J. Chem. 1984, 62, 644) for the synthesis of another glycoside of 45.

SYNTHESIS OF STARTING MATERIAL 47

2-Trimethylsilylethyl 2,6-di-O-acetyl-3-deoxy-3-ethyl-4-O-(2,3,4,6-tetra-O-acetyl-α-D-galactopyranosyl)-β-D-galactopyranoside Compound 6 was deacetylated to give 2-trimethylsilylethyl β-D-galactopyranoside, which was partially protected to give 2-trimethylsilylethyl 3,4-O-isopropylidene-6-O-(2-methoxyisopropyl)-β-D-galactopyranoside. Benzylation of the 2-OH group gave 2-trimethylsilylethyl 2-O-benzyl-3,4-O-isopropylidene-6-O-(2-methoxyisopropyl)-β-D-galactopyranoside which was then hydrolysed under acidic conditions to give 2-trimethylsilylethyl 2-O-benzyl-β-D-galactopyranoside. These steps were performed essentially as described by Catelani et al. (Tetrahedron Lett., 1986, 27, 2307).

Benzylidenation then gave 2-trimethylsilylethyl 2-O-benzyl-4,6-O-benzylidene-β-D-galactopyranoside in an over-all yield of 50% from compound 6. [Acetylation gave 2-trimethylsilylethyl 3-O-acetyl-2-O-benzyl-4,6-O-benzylidene-β-D-galactopyranoside which was submitted to careful analysis: $[\alpha]_D^{23} = -64°$ (c=0.7, CHCl₃) ¹H-nmr ((CDCl₃): δ 5.50 (s, 1H, PhCH), 4.94 and 4.66 (ABq, 2H, J 11.6 Hz, PHCH₂), 4.92 (dd, 1H, J 10.1 Hz, and 3.8 Hz, H-3), 4.49 (d, 1H, J 7.9 Hz, H-1), 4.36 to 4.30 (2H, H-4, H-3), 4.13 to 4.02 (2H, H-6, O—CH₂—CH₂), 3.83 (dd, 1H, J 7.9 Hz, and 10.3 Hz, H-2), 3.61 (m, 1H, O—CH₂—CH₂), 3.49 (bs, 1H, H-5), 1.06 (m, 1H, C—CH₂—Si), 0.04 (s, 9H, Me₃Si)].

Oxidation with methylsulfoxid/oxalyl chloride gave 2-trimethylsilylethyl 2-O-benzyl-4,6-O-benzylidene-β-D-xylohexopyranoside-3-ulose (85%), which was then submitted to a Wittig reaction to give 2-trimethylsilylethyl 2-O-benzyl-4,6-O-benzylidene-3-C-ethylene-β-D-xylo-hexopyranoside (67%). Hydrogenation gave 2-trimethylsilylethyl 2-O-benzyl-4,6-O-benzylidene-3-deoxy-3-C-ethyl-β-D-galactopyranoside as the only diastereomer formed. Reductive opening of the benzylidene ring gave 2-trimethylsilylethyl 2,6-di-O-benzyl-3-deoxy-3-C-ethyl-β-D-galactopyranoside (50%). $[\alpha]_D^{23} = -6°$ (c=1.0, CHCl₃).

¹H-nmr (CDCl₃): δ 4.95 and 4.56 (ABq, 2H, J 11.0 Hz, PhCH₂), 4.62 and 4.55 (ABq, 2H, J 11.9 Hz, PhCH₂), 4.40 (d, 1H, J 7.8 Hz, H-1), 4.04 (m, 1H, O—CH₂—CH₂), 3.89 (bd, 1H, J 1.2 Hz, H-4), 3.7 (dd, 1H, J 10.2 Hz, and 5.5 Hz, H-6), 3.70 (dd, 1H, J 10.0 Hz and 5.0 Hz, H-6), 3.65 to 3.56 (m, 2H, H-5, O—CH₂—CH₂), 3.24 (dd, 1H, J 7.7 Hz and 10.1 Hz), 1.95 to 1.76 (bs, 2H, 4-OH, CH₂—CH₃), 1.45 (m, 2H, H-3, CH₂—CH₃), 1.06 (m, 2H, C—CH₂—Si), 0.94 (bt, 3H, CH₂—CH₃), 0.04 (s, 9H, Me₃Si).

Glycosidation with 2,3,4,6-tetra-O-benzyl-α-D-galactopyranosyl chloride gave the disaccharide derivative 2-trimethylsilylethyl 2,6-di-O-benzyl-3-deoxy-3-C-ethyl-4-O-(2,3,4,6-tetra-O-benzyl-α-D-galactopyranosyl)-β-D-galactopyransoside (85%) followed by hydrogenolytic debenzylation. Acetylation of the hydroxyl groups gave compound 47 (90%): $[\alpha]_D^{23} = -59°$ (c=1.0, CHCl₃).

¹H-nmr ((CDCl₃): δ 5.52 (bd, 1H, J 3.0 Hz, H4'), 5.34 (dd, 1H, J 3.0 Hz and 11.1 Hz, H-3'), 5.26 (dd, 1H, J 3.6 Hz and 11.1 Hz, H-2'), 5.09 (d, 1H, J 3.7 Hz, H-1'), 4.88 (dd, 1H, J 7.6 Hz and 10.8 Hz, H-2), 4.47 to 4.36 (2H, H-5, H-6), 4.38 (d, 1H, J 7.9 Hz, H-1), 4.21 (dd, 1H, J 6.4 Hz and 10.9 Hz, H-6), 4.12 (dd, 1H, J 7.4 Hz and 11.3 Hz, H-6'), 4.04 (dd, 1H, J 6.4 Hz and 10.9 Hz, H-6'), 3.96 (m, 1H, O—CH₂—CH₂), 3.84 (bs, 1H, H-4), 3.68 (bt, 1H, J 6.6 Hz, H-5), 3.53 (m, 1H, O—CH₂—CH₂), 1.70 to 1.40 (m, 3H, CH₂—CH₃, H-3), 1.15 to 0.82 (m, 5H, CH₃—C, C—CH₂—Si), 0.01 (s, 9H, Me₃Si).

¹³C-nmr (CDCl₃): δ 102.0 (C-1), 98.9 (C-1'), 46.9 (C-3), 11.9 (CH₃), −1.3 (Me₃Si)

The final reaction steps were performed essentially as described by Kihlberg et al. (Carbohydr. Res., 152 (1986) 113–130).

We claim:

1. A method for preparing an unprotected hydroxy compound from a protected hydroxy compound of the general formula I

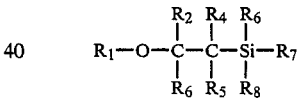

in which

R₁ is the non-hydroxy moiety of a hydroxy compound selected from the group consisting of hydroxy-containing amino acids, peptides containing at least one such acid, and carbohydrates or derivatives thereof;

R₂, R₃, R₄ and R₅ which may be the same or different are hydrogen, C₁₋₄ alkyl or aryl;

and R₆, R₇ and R₈ which may be the same or different are C₁₋₄ alkyl phenyl, substituted phenyl or a carrier in which the compound of formula I is reacted with a Lewis acid followed by reaction with water forming a hydroxy compound of the general formula II

in which R₁ is as defined above.

2. A method according to claim 1 in which R₂, R₃, R₄ and R₅ each are hydrogen.

3. A method according to claim 1 in which R₆, R₇ and R₈ each are methyl.

4. A method according to claim 1 in which the Lewis acid is BF₃, ZnCl₂, FeCl₃, MgBr₂, AlCl₃, SnCl₄, ZnBr₂, TiCl₄., TiF₄, BBr₃, SnBr₄ or TiBr₄.

5. A method according to claim 1 in which R₁ is the non-hydroxy moiety of a hydroxy-containing amino acid forming part of a peptide, and one of $R_6$, $R_7$ and $R_8$ is a carrier.

6. The method of claim 1 in which the carrier is an organic or inorganic, polymeric or macromolecular structure which is attachable to the silicon atom of the compound of formula I.

7. The method of claim 1 in which $R_1$ is a carbohydrate moiety attached to the oxygen atom of Formula I through the 1-carbon atom of the carbohydrate, or a derivative thereof.

8. A method for preparing a compound of the general formula III $$R_1\text{—O—A}$$

in which $R_1$ is the non-hydroxy moiety of hydroxy compound selected from the group consisting of hydroxy-containing amino acids, peptides containing at least one such acid, and carbohydrates or derivatives thereof; and A is an acyl group comprising reacting a protected hydroxy compound of the formula I

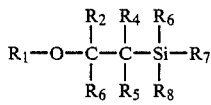

in which $R_1$ is a defined above; and $R_2$, $R_3$, $R_4$, $R_5$, $R_6$, $R_7$ and $R_8$ are as defined in claim 1, with a Lewis acid in the presence of an activated derivative of an acid of the general formula A—OH where S is as defined above.

9. A method according to claim 8 in which $R_2$, $R_3$, $R_4$ and $R_5$ each are hydrogen.

10. A method according to claim 8 in which $R_6$, $R_7$ and $R_8$ each are methyl.

11. A method according to claim 8 in which the Lewis acid is $BF_3$, $ZnCl_2$, $FeCl_3$, $MgBr_2$, $AlCl_3$, $SnCl_4$, $ZnBr_2$, $TiCl_4$, $TiF_4$, $BBr_3$, $SnBr_4$ or $TiBr_4$.

12. A method according to claim 8 in which the activated derivative of the acid of formula A—OH is an activated derivative of a carboxylic acid.

13. A method according to claim 12 in which the activated derivative is an anhydride.

14. A method according to claim 13 in which the anhydride is a symmetric anhydride or a mixed anhydride.

15. A method according to claim 13 in which the anhydride is selected from the group consisting of
Valeric anhydride
Dichlorofluoroacetic anhydride
Butyric anhydride
Isobutyric anhydride
Isovaleric anhydride
Trifluoroacetic anhydride
Acetic anhydride
Trimethylacetic anhydride
Dichloroacetic anhydride
Heptafluorobutyric anhydride
N-butyric anhydride
Nicotinic anhydride
Hexanoic anhydride
Heptanoic anhydride
Chloroacetic anhydride
Benzoic anhydride
Propionic anhydride
3-Methylcrotonic acid anhydride
Crotonic anhydride
Trichloroacetic anhydride
Oleic anhydride
p-Nitrobenzoic anhydride
p-Methoxybenzoic anhydride
p-Trifluoroacetamidobenzoic anhydride
p-Nitrobenzoic-acetic anhydride
Stearic anhydride.

16. The method of claim 8 in which the carrier is an organic or inorganic, polymeric or macromolecular structure which is attachable to the silicon atom of the compound of formula I.

17. The method of claim 8 in which $R_1$ is a carbohydrate moiety attached to the oxygen atom of Formula I through the 1-carbon atom of the carbohydrate, or a derivative thereof.

18. A compound of the general formula IV:

$$R_1\text{—O—X}$$

in which $R_1$ is the non-hydroxy moiety of a hydroxy compound selected from the group consisting of hydroxy-containing amino acids, peptides containing at least one such amino acid and carbohydrates or derivatives thereof; and X is a residue of a Lewis acid.

19. A compound according to claim 18 in which X is selected from the group consisting of $-BF_2$, $-ZnCl$, $-ZnBr$, $-FeCl_2$, $-MgBr$, $-AlCl_2$, and $-SnCl_3$, $-TiCl_3$, $-TiF_3$, $-BBr_2$, $-SnBr_3$ or $-TiBr_3$.

20. The method of claim 18 in which $R_1$ is a carbohydrate moiety attached to the oxygen atom of Formula IV through the 1-carbon atom of the carbohydrate, or a derivative thereof.

21. A method for preparing a compound of formula $R_1$—O—X, where X is a residue of a Lewis acid and $R_1$ is as defined in claim 1, comprising reacting a protected hydroxy compound of the formula I in which $R_1$, $R_2$, $R_3$, $R_4$, $R_5$, $R_6$, $R_7$ and $R_8$ are as defined in claim 1 with a Lewis acid under dry conditions.

22. A compound of the general formula Ia

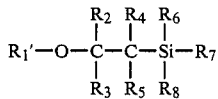

wherein
$R_1'$ is a carbohydrate moiety containing two or more sugar units or a derivative thereof, and
$R_2$, $R_3$, $R_4$, $R_5$, $R_6$, $R_7$ and $R_8$ are as defined in claim 1.

23. A method for preparing a compound of the general formula Ia defined in claim 22 in which a compound of the general formula Ib

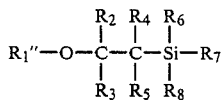

wherein $R_1''$ is a partially protected carbohydrate moiety containing one or more sugar units less than the group $R_1'$ is subjected to a glycosidation reaction followed by removal of the protective groups.

24. A method according to claim 23 in which the glycosidation is carried out by enzymatic or microbial means.

25. The method of claim 22 in which the carrier is an organic or inorganic, polymeric or macromolecular structure which is attachable to the silicon atom of the compound of formula I.

26. A carbohydrate derivative containing one or more sugar units and being acylated in the C-1 and C-2 positions of the reducing sugar unit, wherein the acyl groups in the C-1 and C-2 positions are different.

27. A method for preparing a compound of the general formula V $$R_{10}-Y \qquad V$$

in which $R_{10}$ is a carbohydrate moiety containing one or more sugar units and being attached to Y through the 1-carbon atom, and Y is an alcohol or thiol group in which a carbohydrate derivative containing one or more sugar units and acylated in the C-1 and C-2 positions of the reducing sugar unit, the acyl groups in the C-1 and C-2 positions being different, is reacted with a alcohol or a thiol in the presence of a Lewis acid.

28. A method according to claim 27 in which the alcohol or thiol is selected from partially protected sugars and compounds of the type H—X—R—R' wherein X is oxygen or sulphur, R is selected from the group consisting of alkylene with up to 25 carbon atoms, alkylene with up to 25 carbon atoms with a carbon chain interrupted by a sulfur atom, or aryl, and R' is H, F, Cl, Br, I, CHO, $CH(OR'')_2$, $NO_2$, $NH_2$, OH, SH, COOH, $COOCH_3$, $COOCH_2CH_3$, $CONHNH_2$, or $CON_3$ wherein R'' is $C_{1-4}$ alkyl.

* * * * *